United States Patent
Klein et al.

(10) Patent No.: US 10,721,928 B2
(45) Date of Patent: Jul. 28, 2020

(54) USE OF BIPOLYMER FOR REDUCING THE FORMATION OF A BIOFILM

(71) Applicant: Amsilk GmbH, Planegg/Martinsried (DE)

(72) Inventors: Jens Klein, Pullach I. Isartal (DE); Lin Romer, Ottobrunn (DE); Thomas Scheibel, Bayreuth (DE); Ute Slotta, Munich (DE)

(73) Assignee: Amsilk GmbH, Planegg/Martinsried (DE)

( * ) Notice: Subject to any disclaimer, the term of this patent is extended or adjusted under 35 U.S.C. 154(b) by 0 days.

(21) Appl. No.: 15/767,107

(22) PCT Filed: Oct. 11, 2016

(86) PCT No.: PCT/EP2016/074350
§ 371 (c)(1),
(2) Date: Apr. 9, 2018

(87) PCT Pub. No.: WO2017/064066
PCT Pub. Date: Apr. 20, 2017

(65) Prior Publication Data
US 2019/0069541 A1 Mar. 7, 2019

(30) Foreign Application Priority Data
Oct. 12, 2015 (EP) .................... 15189329

(51) Int. Cl.
| | | |
|---|---|---|
| *A01N 25/34* | (2006.01) | |
| *A01N 63/00* | (2020.01) | |
| *A01N 63/10* | (2020.01) | |
| *A61L 27/22* | (2006.01) | |
| *C07K 14/435* | (2006.01) | |

(52) U.S. Cl.
CPC ............. *A01N 25/34* (2013.01); *A01N 63/00* (2013.01); *A01N 63/10* (2020.01); *A61L 27/227* (2013.01); *C07K 14/43518* (2013.01)

(58) Field of Classification Search
None
See application file for complete search history.

(56) References Cited

U.S. PATENT DOCUMENTS

2009/0162439 A1* 6/2009 Gobin .................... A01N 25/10
424/486

FOREIGN PATENT DOCUMENTS

| WO | 2006008163 A2 | 1/2006 |
| WO | 2011/069643 A2 | 6/2011 |
| WO | 2015/023798 A1 | 2/2015 |

OTHER PUBLICATIONS

Carlson, R. et al., J. Biomater. Sci. Polymer Edn, 2008, vol. 19, pp. 1035-1048.*
Willcox, M. et al., J. Appl. Microbiol. 2008 vol. 105, pp. 1817-1825.*
International Search Report in PCT/EP2016/074350, dated Dec. 19, 2016, 4 pages.
Carlson et al., "Anti-Biofilm Properties of Chitosan-Coated Surfaces," Journal of Biomaterials Science, Polymer Ed., vol. 19, No. 8, 1 Jan. 2008, 1035-1046.
Costa et al., "Covalent Immobilization of Antimicrobial Peptides (AMPs) onto Biomatierla Surfaces," Acta Biomaterialia, Elseviewr, Amsterdam, Nl, vol. 7, No. 4, 1 Nov. 2010, 1431-1440.
Willcox et al., "A Novel Cationic-Peptide Coating for the Prevention of Microbial Colonization on Contact Lenses," Journal of Applied Microbiology, vol. 105, No. 6, 1 Dec. 2008, 1817-1825.
Yoshinari et al., "Prevention of Biofilm Formation on Titanium Surfaces Modified with Conjugated Molecules Comprised of Antimicrobial and Titanium-Binding Peptides," Biofueling, vol. 26, No. 1, 16 Oct. 2009, 103-110.

* cited by examiner

*Primary Examiner* — Heidi Reese
(74) *Attorney, Agent, or Firm* — Kilpatrick Townsend & Stockton LLP (57) ABSTRACT

The present invention relates to the use of a biopolymer for reducing the formation of a biofilm, preferably on a substrate, whereby the biopolymer is preferably a polypeptide, such as recombinant spider silk polypeptide. The present invention further relates to methods for producing a substrate which reduces the formation of a biofilm on a surface of said substrate.

14 Claims, 1 Drawing Sheet
Specification includes a Sequence Listing.

SEQUENCE LISTING

```
<160> NUMBER OF SEQ ID NOS: 8

<210> SEQ ID NO 1
<211> LENGTH: 24
<212> TYPE: PRT
<213> ORGANISM: Artificial Sequence
<220> FEATURE:
<223> OTHER INFORMATION: synthetic
<220> FEATURE:
<221> NAME/KEY: DOMAIN
```

```
<222> LOCATION: (1)..(24)
<223> OTHER INFORMATION: Module A (ADF-3)

<400> SEQUENCE: 1

Gly Pro Tyr Gly Pro Gly Ala Ser Ala Ala Ala Ala Ala Gly Gly
1               5                   10                  15

Tyr Gly Pro Gly Ser Gly Gln Gln
            20

<210> SEQ ID NO 2
<211> LENGTH: 35
<212> TYPE: PRT
<213> ORGANISM: Artificial Sequence
<220> FEATURE:
<223> OTHER INFORMATION: synthetic
<220> FEATURE:
<221> NAME/KEY: DOMAIN
<222> LOCATION: (1)..(35)
<223> OTHER INFORMATION: Module C (ADF-4)

<400> SEQUENCE: 2

Gly Ser Ser Ala Ala Ala Ala Ala Ala Ala Ser Gly Pro Gly Gly
1               5                   10                  15

Tyr Gly Pro Glu Asn Gln Gly Pro Ser Gly Pro Gly Gly Tyr Gly Pro
            20                  25                  30

Gly Gly Pro
        35

<210> SEQ ID NO 3
<211> LENGTH: 35
<212> TYPE: PRT
<213> ORGANISM: Artificial Sequence
<220> FEATURE:
<223> OTHER INFORMATION: synthetic
<220> FEATURE:
<221> NAME/KEY: DOMAIN
<222> LOCATION: (1)..(35)
<223> OTHER INFORMATION: Module Cc

<400> SEQUENCE: 3

Gly Ser Ser Ala Ala Ala Ala Ala Ala Ala Ser Gly Pro Gly Gly
1               5                   10                  15

Tyr Gly Pro Glu Asn Gln Gly Pro Cys Gly Pro Gly Gly Tyr Gly Pro
            20                  25                  30

Gly Gly Pro
        35

<210> SEQ ID NO 4
<211> LENGTH: 20
<212> TYPE: PRT
<213> ORGANISM: Artificial Sequence
<220> FEATURE:
<223> OTHER INFORMATION: synthetic
<220> FEATURE:
<221> NAME/KEY: DOMAIN
<222> LOCATION: (1)..(20)
<223> OTHER INFORMATION: Module Q (ADF-3)

<400> SEQUENCE: 4

Gly Pro Gly Gln Gln Gly Pro Gly Gln Gln Gly Pro Gly Gln Gln Gly
1               5                   10                  15

Pro Gly Gln Gln
            20

<210> SEQ ID NO 5
```

```
<211> LENGTH: 124
<212> TYPE: PRT
<213> ORGANISM: Artificial Sequence
<220> FEATURE:
<223> OTHER INFORMATION: based on ADF-3
<220> FEATURE:
<221> NAME/KEY: DOMAIN
<222> LOCATION: (1)..(124)
<223> OTHER INFORMATION: NR3 (ADF-3)

<400> SEQUENCE: 5

Gly Ala Ala Ser Ala Ala Val Ser Val Gly Tyr Gly Pro Gln Ser
1               5                   10                  15

Ser Ser Ala Pro Val Ala Ser Ala Ala Ala Ser Arg Leu Ser Ser Pro
            20                  25                  30

Ala Ala Ser Ser Arg Val Ser Ser Ala Val Ser Ser Leu Val Ser Ser
                35                  40                  45

Gly Pro Thr Asn Gln Ala Ala Leu Ser Asn Thr Ile Ser Ser Val Val
    50                  55                  60

Ser Gln Val Ser Ala Ser Asn Pro Gly Leu Ser Gly Cys Asp Val Leu
65                  70                  75                  80

Val Gln Ala Leu Leu Glu Val Val Ser Ala Leu Val Ser Ile Leu Gly
                85                  90                  95

Ser Ser Ser Ile Gly Gln Ile Asn Tyr Gly Ala Ser Ala Gln Tyr Thr
                100                 105                 110

Gln Met Val Gly Gln Ser Val Ala Gln Ala Leu Ala
            115                 120

<210> SEQ ID NO 6
<211> LENGTH: 109
<212> TYPE: PRT
<213> ORGANISM: Artificial Sequence
<220> FEATURE:
<223> OTHER INFORMATION: based on ADF-4
<220> FEATURE:
<221> NAME/KEY: DOMAIN
<222> LOCATION: (1)..(109)
<223> OTHER INFORMATION: NR4 (ADF-4)

<400> SEQUENCE: 6

Gly Ala Tyr Gly Pro Ser Pro Ser Ala Ser Ala Ser Val Ala Ala Ser
1               5                   10                  15

Arg Leu Ser Ser Pro Ala Ala Ser Ser Arg Val Ser Ser Ala Val Ser
            20                  25                  30

Ser Leu Val Ser Ser Gly Pro Thr Asn Gly Ala Ala Val Ser Gly Ala
                35                  40                  45

Leu Asn Ser Leu Val Ser Gln Ile Ser Ala Ser Asn Pro Gly Leu Ser
    50                  55                  60

Gly Cys Asp Ala Leu Val Gln Ala Leu Leu Glu Leu Val Ser Ala Leu
65                  70                  75                  80

Val Ala Ile Leu Ser Ser Ala Ser Ile Gly Gln Val Asn Val Ser Ser
                85                  90                  95

Val Ser Gln Ser Thr Gln Met Ile Ser Gln Ala Leu Ser
            100                 105

<210> SEQ ID NO 7
<211> LENGTH: 136
<212> TYPE: PRT
<213> ORGANISM: artificial
<220> FEATURE:
<223> OTHER INFORMATION: synthetic
<220> FEATURE:
```

<221> NAME/KEY: domain
<222> LOCATION: (1)..(136)
<223> OTHER INFORMATION: derived from Latrodectus hesperus

<400> SEQUENCE: 7

Met Gly Gln Ala Asn Thr Pro Trp Ser Ser Lys Ala Asn Ala Asp Ala
1               5                   10                  15

Phe Ile Asn Ser Phe Ile Ser Ala Ala Ser Thr Gly Ser Phe Ser
            20                  25                  30

Gln Asp Gln Met Glu Asp Met Ser Leu Ile Gly Asn Thr Leu Met Ala
            35                  40                  45

Ala Met Asp Asn Met Gly Gly Arg Ile Thr Pro Ser Lys Leu Gln Ala
    50                  55                  60

Leu Asp Met Ala Phe Ala Ser Ser Val Ala Glu Ile Ala Ala Ser Glu
65                  70                  75                  80

Gly Gly Asp Leu Gly Val Thr Thr Asn Ala Ile Ala Asp Ala Leu Thr
                85                  90                  95

Ser Ala Phe Tyr Gln Thr Thr Gly Val Val Asn Ser Arg Phe Ile Ser
            100                 105                 110

Glu Ile Arg Ser Leu Ile Gly Met Phe Ala Gln Ala Ser Ala Asn Asp
        115                 120                 125

Val Tyr Ala Ser Ala Gly Ser Gly
        130                 135

<210> SEQ ID NO 8
<211> LENGTH: 137
<212> TYPE: PRT
<213> ORGANISM: artificial
<220> FEATURE:
<223> OTHER INFORMATION: synthetic
<220> FEATURE:
<221> NAME/KEY: domain
<222> LOCATION: (1)..(137)
<223> OTHER INFORMATION: derived from Latrodectus hesperus

<400> SEQUENCE: 8

Met Gly Gln Ala Asn Thr Pro Trp Ser Ser Lys Glu Asn Ala Asp Ala
1               5                   10                  15

Phe Ile Gly Ala Phe Met Asn Ala Ala Ser Gln Ser Gly Ala Phe Ser
            20                  25                  30

Ser Asp Gln Ile Asp Asp Met Ser Val Ile Ser Asn Thr Leu Met Ala
            35                  40                  45

Ala Met Asp Asn Met Gly Gly Arg Ile Thr Gln Ser Lys Leu Gln Ala
    50                  55                  60

Leu Asp Met Ala Phe Ala Ser Ser Val Ala Glu Ile Ala Val Ala Asp
65                  70                  75                  80

Gly Gln Asn Val Gly Ala Ala Thr Asn Ala Ile Ser Asp Ala Leu Arg
                85                  90                  95

Ser Ala Phe Tyr Gln Thr Thr Gly Val Val Asn Asn Gln Phe Ile Thr
            100                 105                 110

Gly Ile Ser Ser Leu Ile Gly Met Phe Ala Gln Val Ser Gly Asn Glu
        115                 120                 125

Val Ser Tyr Ser Ser Ala Gly Ser Gly
        130                 135

USE OF BIPOLYMER FOR REDUCING THE FORMATION OF A BIOFILM

CROSS REFERENCE TO RELATED APPLICATIONS

This application is a U.S. National phase of PCT/EP2016/074350, international filing date of Oct. 11, 2016, which claims priority to EP 15189329.4, filed Oct. 12, 2015, the disclosures of which are incorporated herein by reference for all purposes.

REFERENCE TO SUBMISSION OF A SEQUENCE LISTING AS A TEXT FILE

The Sequence Listing written in file US_sequence_listing_ST25_1082266.txt created on Apr. 5, 2018, 6.84 bytes, machine format IBM-PC, MS-Windows operating system, is hereby incorporated by reference in its entirety for all purposes.

The present invention relates to the use of a biopolymer for reducing the formation of a biofilm. The present invention further relates to methods for producing a substrate which reduces the formation of a biofilm on a surface of said substrate.

BACKGROUND OF THE INVENTION

A biofilm is build up by microorganisms. In a biofilm, microbial cells stick to each other and/or to a surface. These cells generally resemble adherent cells which are often embedded within a self-produced matrix of extracellular polymeric substance (EPS). The self-produced matrix of extracellular polymeric substance can also be designated as microbial slime. It is a polymeric conglomeration generally composed of extracellular DNA, proteins, and/or polysaccharides. Microorganisms form a biofilm in response to many factors, which may include cellular recognition of specific or non-specific attachment sites on a surface, nutritional cues, or by exposure to specific molecules and/or stimuli. When a cell switches to the biofilm mode of growth, it undergoes a phenotypic shift in behavior in which several genes are differently regulated.

Biofilms preferentially develop on inert surfaces including those of everyday and household items as well as on medical devices. Biofilms may form on polymeric materials, metals, glass, and ceramics, among others. Exposure to such microorganisms for instance through skin-surface contact may result in infections that compromise the health. Biofilms may form on any number of items with which persons come into contact such as: hygiene products, medical devices, household appliances, tap ware and so forth. Controlling formation of biofilms could result in less infection of individuals.

Biofilm formation has further important public health implications. Drinking water systems and waste water systems are known to harbor biofilms, even though these environments often contain disinfectants. Any system providing an interface between a surface and a fluid or gas has the potential for biofilm development. Ventilation systems as well as air condition systems such as water cooling towers for air conditioners are well-known to pose public health risks from biofilm formation, as episodic outbreaks of infections caused by *Legionella* attest. Turbulent fluid flow over the surface does not provide protection. Biofilms can form in conduits where flowing water or other fluids pass, with the effects of altering flow characteristics and passing planktonic organisms downstream. Industrial fluid processing operations have experienced mechanical blockages, impedance of heat transfer processes, and biodeterioration of fluid-based industrial products, all attributable to biofilms. Biofilms have been identified in flow conduits such as hemodialysis tubing, and in water distribution conduits. Biofilms have also been identified to cause biofouling in selected municipal water storage tanks, private wells and drip irrigation systems.

Microbial infection, and the subsequent formation of biofilms remains one of the most serious complications in several areas, particularly in medical devices, drugs, health care and hygienic applications, drinking water systems, water purification systems, hospital and dental surgery equipment, textiles, food packaging and food storage systems. Since the difficulties associated with eliminating biofilm-based infections are well-recognized, a number of agents have been tested to treat surfaces or fluids bathing surfaces to prevent or impair biofilm formation.

Preventing or impairing biofilm formation by undesirable microorganisms traditionally requires the use of dispersants, surfactants, enzymes, antimicrobial agents, biocides, specific metals, and/or chemicals. However, the agents for preventing or impairing biofilm formation on the market, e.g. antimicrobial agents or metals such as silver, have been reported to be expensive, not permanent, harmful to health, harmful to the environment, and to require a laborious process for their manufacture and application. In addition, many agents used in this context cannot be sterilized. Antibiotics, for example, are often not active anymore after undergoing sterilization processes. Moreover, many agents for preventing or impairing biofilm formation, e.g. chemical additives, are not suitable in medical applications in view of their side effects. In addition, any agent used to prevent or impair biofilm formation that will be exposed to individuals must be safe to the user. Certain biocidal agents, in quantities sufficient to interfere with biofilms, also can damage host tissues. Thus, it is advantageous for the biofilm resistant compound to function not as a biocide, but to render surfaces unsuitable for adhesion and colonization by microorganisms. Such a compound does not rely on a "kill mechanism" for the prevention of biofilms, but on creating an environment not conducive to biofilm formation.

Based on the above, there is a need for new agents/substrates which can be used for preventing or impairing biofilm formation, e.g. agents/substrates, which are cost-effective, stable, sterilizable, safe, and free of side effects. Natural substances or nature-identical substances for this purpose would be highly desirable as they are usually well tolerated by human beings and animals. However, such natural substances usually resemble perfect breeding soils for microbes—resulting in the opposite of the desired effect.

The inventors of the present invention surprisingly found a biopolymer which has the above-mentioned properties and which is, thus, very suitable for the avoidance or reduction of biofilm formation. They surprisingly found that biofilm formation can be avoided or reduced by coating a surface of a substrate with the biopolymer or by incorporating the biopolymer into a substrate as a whole. The mechanism by which the present invention prolongates/hinders the formation and growth of biofilms is by creating a surface with the biopolymer, wherein microorganisms associated with biofilms do not readily adhere or colonize.

SUMMARY OF THE INVENTION

In a first aspect, the present invention relates to the use of a biopolymer for avoiding or reducing the formation of a biofilm.

In a second aspect, the present invention relates to a method for producing a substrate which avoids or reduces the formation of a biofilm on a surface of said substrate comprising the steps of:
(i) providing a composition comprising a biopolymer and a solvent, and
(ii) coating the composition onto the surface of said substrate.

In a third aspect, the present invention relates to a method for producing a substrate which avoids or reduces the formation of a biofilm on a surface of said substrate comprising the steps of:
(i) providing a composition comprising a biopolymer and a solvent, and
(ii) forming said substrate from the composition.

DETAILED DESCRIPTION OF THE INVENTION

Before the present invention is described in detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

Preferably, the terms used herein are defined as described in "A multilingual glossary of biotechnological terms: (IUPAC Recommendations)", Leuenberger, H. G. W, Nagel, B. and Kolbl, H. eds. (1995), Helvetica Chimica Acta, CH-4010 Basel, Switzerland).

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step.

Several documents are cited throughout the text of this specification. Each of the documents cited herein (including all patents, patent applications, scientific publications, manufacturer's specifications, instructions, GenBank Accession Number sequence submissions etc.), whether supra or infra, is hereby incorporated by reference in its entirety. Nothing herein is to be construed as an admission that the invention is not entitled to antedate such disclosure by virtue of prior invention.

In the following, the elements of the present invention will be described. These elements are listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments which combine the explicitly described embodiments with any number of the disclosed and/or preferred elements. Furthermore, any permutations and combinations of all described elements in this application should be considered disclosed by the description of the present application unless the context indicates otherwise.

The term "comprise" or variations such as "comprises" or "comprising" according to the present invention means the inclusion of a stated integer or group of integers but not the exclusion of any other integer or group of integers. The term "consisting essentially of" according to the present invention means the inclusion of a stated integer or group of integers, while excluding modifications or other integers which would materially affect or alter the stated integer. The term "consisting of" or variations such as "consists of" according to the present invention means the inclusion of a stated integer or group of integers and the exclusion of any other integer or group of integers.

As mentioned above, there is a need for new agents/substrates which can be used for preventing or impairing biofilm formation, e.g. agents/substrates, which are cost-effective, stable, sterilizable, safe, non-toxic and free of side effects. Natural substances or nature-identical substances for this purpose would be highly desirable as they are usually well tolerated by human beings and animals.

The inventors of the present invention surprisingly found a biopolymer which has the above-mentioned properties and which is, thus, very suitable for the avoidance or reduction of biofilm formation. They surprisingly found that biofilm formation can be avoided or reduced by coating a surface of a substrate with the biopolymer or by incorporating the biopolymer into a substrate as a whole. This was amazing because the biopolymer itself comprises components (e.g. amino acids) which generally serve as a breeding ground for biofilm-forming microorganisms. The mechanism by which the present invention prolongs/hinders the formation and growth of biofilms is by creating a surface with the biopolymer, wherein microorganisms associated with biofilms do not readily adhere or colonize. In other words, the biopolymer renders the surface of a substrate which is usually prone to the formation of a biofilm unsuitable for adhesion and colonization by microorganisms. The biopolymer does not rely on a "kill mechanism" for the avoidance or reduction of biofilms. It rather avoids or reduces biofilm formation by interfering with a microorganism's ability to attach to a surface.

Thus, in a first aspect, the present invention relates to the use of a biopolymer for avoiding or reducing the formation of a biofilm. Said use may be an in vitro or in vivo use.

The term "biopolymer", as used in the context of the present invention, encompasses any biopolymer which avoids or reduces the formation of a biofilm. As mentioned above, the biopolymer does not rely on a "kill mechanism" for the avoidance or reduction of biofilms, but on creating an environment not conducive to biofilm formation. The term "biopolymer", as used herein, further refers to a molecule which is preferably formed from repeating building blocks similar to nature. The biopolymer may be a polypeptide, e.g. a recombinant polypeptide. Said polypeptide comprises repeating building blocks made of amino acids.

Unless otherwise indicated, the terms "polypeptide" and "protein" are used interchangeably herein and mean any peptide-linked chain of amino acids, regardless of length or post-translational modification. In addition, the terms "repeating building block", "repeating unit", "repetitive unit", or "repeat unit" are interchangeable used in the context of the present invention.

The term "avoiding the formation of a biofilm", as used herein, means that no biofilm is formed as compared to a corresponding situation in which no biopolymer is present. The term "reducing the formation of a biofilm", as used herein, means that less biofilm is formed as compared to a corresponding situation in which no biopolymer is present. The formation of a biofilm may be reduced by at least 1%, 5%, 10%, 20%, 30%, 40%, 50%, 60%, 70%, 80%, 90%, 95%, 98% or 99%, or by 100% as compared to a corresponding situation in which no biopolymer is present. Preferably, the formation of a biofilm is reduced by at least 10%. More preferably, the formation of a biofilm is reduced by at least 20%. Even more preferably, the formation of a biofilm is reduced by at least 30%. Most preferably, the formation of a biofilm is reduced by at least 90%, e.g. 100%. The skilled person can experimentally easily determine whether the formation of a biofilm is avoided or reduced, e.g. by cell count measurements, optical density (OD) measurements, or other methods such as polymerase chain reaction (PCR). Preferably, cell count measurements are used. In this respect, it is referred to the experimental section.

In one preferred embodiment, the formation of the biofilm is avoided or reduced on a (at least one) surface of a substrate. The term "the formation of the biofilm is avoided on a surface of a substrate", as used herein, means that no biofilm is formed as compared to a surface of a substrate not comprising the biopolymer. The term "the formation of the biofilm is reduced on a surface of a substrate", as used herein, means that less biofilm is formed as compared to a surface of a substrate not comprising the biopolymer. The formation of the biofilm on a surface of a substrate may be reduced by at least 1%, 5%, 10%, 20%, 30%, 40%, 50%, 60%, 70%, 80%, 90%, 95%, 98% or 99%, or by 100% as compared to a surface of a substrate not comprising the biopolymer. Preferably, the formation of the biofilm on a surface of a substrate is reduced by at least 10%. More preferably, the formation of the biofilm on a surface of a substrate is reduced by at least 20%. Even more preferably, the formation of a biofilm is reduced by at least 30%. Most preferably, the formation of the biofilm on a surface of a substrate is reduced by at least 90%, e.g. 100%. In case the substrate does not comprise the biopolymer of the invention, i.e. a biopolymer which avoids or reduces the formation of a biofilm, it may, however, comprise another biopolymer not having this effect.

The skilled person can easily determine experimentally whether the formation of the biofilm is avoided or reduced on a surface of a substrate, e.g. by cell count measurements, optical density (OD) measurements, or other methods such as polymerase chain reaction (PCR). In this respect, we like to refer to the experimental section. Preferably, cell count measurements are used.

For example, a surface of a substrate is coated with a biopolymer. The surface of said substrate is then contacted with a microbial solution. As a control, an uncoated substrate is used. The coated substrate and the uncoated substrate (control) are incubated with the microbial solution under the same conditions usually allowing the formation of a biofilm, e.g. between 5 to 36 hours and/or between 20° C. (room temperature) and 35° C. After the removal of the microbial solution from the coated substrate and the uncoated substrate (control), the number of microorganism grown on the surface of the coated substrate and the uncoated substrate (control) is determined and compared with each other. In an alternative approach, a substrate comprising a biopolymer is produced. The surface of the substrate comprising the biopolymer is then contacted with a microbial solution. As a control, a substrate which does not comprise a biopolymer is used. The substrate comprising the biopolymer and the substrate which does not comprise the biopolymer (control) are incubated with the microbial solution under the same conditions usually allowing the formation of a biofilm, e.g. between 5 to 36 hours and/or between 20° C. (room temperature) and 35° C. After the removal of the microbial solution from the substrate comprising the biopolymer and the substrate which does not comprise the biopolymer (control), the number of microorganism grown on the surface of the substrate comprising the biopolymer and the substrate which does not comprise the biopolymer (control) is determined and compared with each other.

The term "biofilm", as used herein, means an aggregate of microorganisms in which cells adhere to each other and/or to a surface. Said cells are frequently embedded within a self-produced matrix of extracellular polymeric substance (EPC). The self-produced matrix of extracellular polymeric substance is also referred to as slime. The "biofilm" can alternatively be defined as a conglomerate of microorganisms that (predominantly) forms at the interface between a liquid phase and a substrate or at the interface between a gaseous phase and a substrate. The conglomerate of microorganisms preferably forms in aqueous or humid environments at the interphase between a liquid phase and a substrate or at the interface between a gaseous phase and a substrate. The biofilm, thus, usually forms at the surface of a substrate. The term "aqueous environment", as used herein, refers to a liquid phase comprising water. The term "humid environment", as used herein, refers to a gaseous phase comprising water vapor.

In one embodiment, the microorganisms comprised in the biofilm are selected from the group consisting of bacteria, fungi, algae, and protozoa, or any combination thereof. It is preferred that the combination predominantly consists of bacteria. Preferably, the bacteria comprised in the biofilm are from the genus *Escherichia, Pseudomonas, Bacillus*, and/or *Staphylococcus*. The bacteria may be gram positive species (e.g. *Bacillus* or *Staphylococcus*) and/or gram negative species (e.g. *Escherichia* or *Pseudomonas*).

The term "surface", as used herein, refers to any surface which is prone to biofilm formation and/or adhesion of microorganisms. The term "surface", as used herein, further refers to any surface on which a biofilm can form. The surface may be a solid surface. The solid surface is, for instance, found in bathrooms, e.g. fixtures, sinks, bathtubs, toilet bowls, and rinse water reservoirs, in cooling towers, in water treatment plants, in water tanks, in dairy, food processing plants, in chemical or pharmaceutical process plants, in hospital facilities, in facilities for doctor's surgeries, in medical offices, in operating rooms or in medical devices (e.g. catheters, orthopedic devices, or implants). A biofilm prone surface may be smooth, structured or irregular. A biofilm prone surface may also be porous. A porous surface can, for instance, be present in filters, e.g. membrane filters or textiles. The term "surface," as used herein, also refers to any surface (whether in a homely, an industrial, or a medical setting) that provides an interphase between a liquid phase and a substrate or that provides an interphase between a gaseous phase and a substrate. The surface permits at least intermittent contact between the substrate and the fluid or gas. Fluids or gases contacting the surface can be stagnant or flowing, and can flow intermittently or continuously, with laminar or turbulent or mixed rheologies. A surface upon which a biofilm forms can be dry at times with sporadic fluid contact, or can have any degree of fluid exposure including total immersion. Fluid contact with the surface can take place via aerosols or other means for air-borne fluid transmission.

The term "substrate", as used herein, means any substrate having a surface which is prone to biofilm formation and/or adhesion of microorganisms. The term "substrate", as used herein, further refers to any substrate having a surface on which a biofilm can form. The substrate may be a solid substrate.

In one embodiment, the substrate is a device. The device may be selected from the group consisting of a medical device, a drinking water device, a wastewater treatment device, a heating device, a ventilation device, and an air condition device. The term "medical device", as used herein, refers to a non-naturally occurring object that is used to examine and/or treat a subject, that is inserted or implanted in a subject, or that is applied to a surface of a subject. An implantable device is one intended to be completely imbedded in the body without any structure left outside the body (e.g., heart valve). An insertable device is one that is partially imbedded in the body but has a part intended to be external (e.g., a catheter or a drain). Medical devices can be intended for short-term or long-term residence where they are positioned. A hip implant is intended for several years of use, for example. By contrast, a tissue expander may only be needed for a few months, and is removed thereafter. Insertable devices tend to remain in place for shorter times than implantable devices, in part because they come into more contact with microorganisms that can colonize them. The subject may be a human or an animal.

In one preferred embodiment, the medical device is selected from the group consisting of an extracorporeal medical device, an implant, and a catheter. The term "implant", as used herein, refers to any object intended for placement in a human or animal body that is not a living tissue. Implants include naturally derived objects that have been processed so that their living tissues have been devitalized. As an example, bone grafts can be processed so that their living cells are removed, but so that their shape is retained to serve as a template for ingrowth of bone from a host. As another example, naturally occurring coral can be processed to yield hydroxyapatite preparations that can be applied to the body for certain orthopedic and dental therapies. An implant can also be an article comprising artificial components. The term "implant" can be applied to the entire spectrum of medical devices intended for placement in a human or animal body. The implant is preferably selected from the group consisting of a stent, a cochlea implant, a microchip implant, a dental implant, and a soft tissue implant, preferably a silicone implant, more preferably a breast implant. In addition, the extracorporeal medical device is preferably selected from the group consisting of a life support machine, a heart-lung machine and a dialysis device. In one embodiment, the substrate is selected from the group consisting of a synthetic inert substrate, an inorganic inert substrate, and a naturally occurring substrate. The term "synthetic inert substrate", as used in the context of the present invention, refers to a substrate that has been manufactured or otherwise created by human beings, as opposed to those occurring in nature. The word "synthetic" also means artificially put together in the context of the present invention. The term "inorganic inert substrate", as used in the context of the present invention, refers to a substrate that does not contain hydrocarbon as the principal element (excepting carbonates, cyanides, and cyanates), that is, matter other than plant or animal, i.e. not of biological origin. The term "naturally occurring substrate", as used in the context of the present invention, refers to a substrate which exists in nature, which may, however, be modified and further processed, e.g. by bleaching, washing, stretching, spinning etc., as long as the modification does not significantly alter the polymer backbone of the substrate.

In one preferred embodiment, (i) the synthetic inert substrate is selected from the group consisting of polyester, polystyrene, polyamide (PA), polyaramid, polytetrafluoroethylene (PTFE), polyethylene (PE), polypropylene (PP), polyurethane (PU), silicone, a mixture of polyurethane and polyethylenglycol (elastane), ultra high molecular weight polyethylene (UHMWPE), and high-performance polyethylene (HPPE), (ii) the inorganic inert substrate is selected from the group consisting of, glass, carbon, ceramic, metal, sapphire, diamond, and semiconductor, or (iii) the naturally occurring substrate is selected from the group consisting of keratin, collagen, cellulose, cotton, teeth, bone, skin, hair, nails, silk, and tissue. In a more preferred embodiment, the naturally occurring material is silk, e.g. spider silk. The naturally occurring substrate may also a transplant. The transplant may be selected from the group consisting of a heart transplant, a kidney transplant, and a liver transplant. The synthetic inert substrate, the inorganic inert substrate or the naturally occurring substrate may have the form of a foil, or may have the form of a fiber, a thread comprising the fiber, a twisted yarn comprising the fiber, or a fabric/textile comprising the fiber. For example, the synthetic inert substrate may be a silicone foil or a polyester fabric/textile. The naturally occurring substrate may be a cotton fabric/textile.

In one embodiment, the biopolymer is in the form of a coating. In one preferred embodiment, the biopolymer is coated on the (at least one) surface of the substrate. In particular, the biopolymer is coated on the (at least one) surface of the substrate and thereby avoids or reduces biofilm formation thereon. The term "coating", as used herein, refers to any layer covering a surface. The biopolymer to be coated can be in form of an aerosol, a liquid, a paste, a semi-solid, or a solid. In addition, the coating can be applied as a hydrogel, an aerosol, or a liquid and solidifies into a solid coating. It is preferred that the coating completely covers the (at least one) surface of the substrate. The coating has preferably a thickness of between 1 nm and 1000 rpm, preferably 40 nm and 50 μm, more preferably between 0.1 μm and 10 μm and most preferably between 0.5 μm and 5 μm. The coating can be achieved by dip coating, and/or spray coating. The coating is preferably a film. In one embodiment, the coating is formed from a composition comprising a biopolymer and a solvent. The composition can be a solution, a suspension, and/or an emulsion. The composition can also be a hydrogel. The solution may be an aqueous solution, a buffered aqueous solution, or an organic solution. The solvent may be water ($H_2O$), an aqueous buffer, or an organic solvent. The organic solvent may be selected from the group consisting of formic acid and hexafluorisopropanol (HFIP). The concentration of the biopolymer in the composition, e.g. solution, may be in the range of 0.1% (w/v) to 30% (w/v). Preferably, the concentration of the biopolymer in the composition, e.g. solution, is in the range of 0.5% (w/v) to 20% (w/v). More preferably, the concentration of the biopolymer in the composition, e.g. solution, is in the range of 0.5% (w/v) to 10% (w/v). Most preferably, the concentration of the biopolymer in the composition, e.g. solution, is in the range of 0.8% (w/v) to 5% (w/v).

As mentioned above, in one embodiment, the biopolymer is in the form of a coating. In particular, the biopolymer is coated on the (at least one) surface of the substrate and thereby avoids or reduces biofilm formation thereon. In one alternative embodiment, the substrate comprises the biopolymer. In particular, the biopolymer is comprised in the substrate and thereby avoids or reduces biofilm formation thereon. The substrate may comprise at least 0.1% (w/v), 1% (w/v), 10% (w/v), 20% (w/v), 30% (w/v), 40% (w/v), 50% (w/v), 60% (w/v), 70% (w/v), 80% (w/v), 90% (w/v), 95% (w/v), 98% (w/v), 99% (w/v), or 100% (w/v) of the biopolymer. Preferably, the substrate comprises at least 1% (w/v)

of the biopolymer. More preferably, the substrate comprises at least 2% (w/v) of the biopolymer. Even more preferably, the substrate comprises at least 10% (w/v) of the biopolymer. Most preferably, the substrate comprises at least 90% (w/v), e.g. 100% (w/v), of the biopolymer. In the latter case, the substrate consists of the biopolymer. The substrate comprising the biopolymer may be selected from the group consisting of a fiber, a thread comprising the fiber, a twisted yarn comprising the fiber, a fabric/textile comprising the fiber. In an alternative embodiment, the substrate does not comprise a biopolymer. In case the substrate does not comprise the biopolymer of the invention, i.e. a biopolymer which avoids or reduces the formation of a biofilm, it may, however, comprise another biopolymer not having this effect.

In one embodiment, the biopolymer is a polypeptide, preferably a recombinant polypeptide. The polypeptide may consist of between 6 to 3000 amino acids, more preferably of between 30 to 1500 amino acids, even more preferably of between 250 to 1200 amino acids, and most preferably of between 500 to 1000 amino acids. Preferably, the polypeptide comprises at least two identical repetitive units. More preferably, the polypeptide comprises between 2 to 100 repetitive units, i.e. at least 2, 3, 4, 5, 6, 7, 8, 9, 10, 11, 12, 13, 14, 15, 16, 17, 18, 19, 20, 21, 22, 23, 24, 25, 26, 27, 28, 29, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 repetitive units. The repetitive units in the polypeptide may be the same (identical) or different. It is preferred that the same (identical) repetitive unit is used in the polypeptide at least 2 times. It is further preferred that the polypeptide comprises or consists of at least 50%, 60%, 65%, 70%, 75%, 80%, 85%, 90%, preferably at least 95% and more preferably 100% of repetitive units.

In one preferred embodiment, the biopolymer is a silk polypeptide, preferably a recombinant silk polypeptide. The silk polypeptide may be a spider silk polypeptide, e.g. a major ampullate silk polypeptide such as a dragline silk polypeptide, a minor ampullate silk polypeptide, or a flagelliform silk polypeptide of an orb-web spider (e.g. Araneidae or Araneoids), an insect silk polypeptide, a mussel byssus silk polypeptide, or a mixture thereof. The orb-web spider may be selected from the group consisting of *Araneus diadematus, Nephila clavipes,* and *Latrodectus hesperus.* The insect silk polypeptide may be of Lepidoptera, particularly Bombycidae such as *Bombyx mori.* The insect silk polypeptide may also be of Hymenoptera, particularly Apoidea such as Anthophila.

Preferably, the biopolymer is a (recombinant) silk polypeptide comprising at least two identical repetitive units. It is preferred that the repetitive units are independently selected from the group consisting of module A (SEQ ID NO: 1) or variants thereof, module C (SEQ ID NO: 2) or variants thereof, module $C^{Cys}$ (SEQ ID NO: 3), and module Q (SEQ ID NO: 4) or variants thereof. Module $C^{Cys}$ (SEQ ID NO: 3) is a variant of module C (SEQ ID NO: 2). In this module, the amino acid S (Ser) at position 25 has been replaced by the amino acid C (Cys).

A module A, C, or Q variant differs from the reference module A, C, or Q from which it is derived by up to 1, 2, 3, 4, 5, 6, 7, 8, 9, 10, 11, 12, 13, 14, or 15 amino acid changes in the amino acid sequence (i.e. substitutions, additions, insertions, deletions, N-terminal truncations and/or C-terminal truncations). Such a module variant can alternatively or additionally be characterised by a certain degree of sequence identity to the reference module from which it is derived. Thus, a module A, C, or Q variant has a sequence identity of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or even 99.9% to the respective reference module A, C, or Q. Preferably, the sequence identity is over a continuous stretch of at least 5, 10, 15, 18, 20, 24, 27, 28, 30, 34, 35, or more amino acids, preferably over the whole length of the respective reference module A, C, or Q.

It is particularly preferred that the sequence identity is at least 80% over the whole length, is at least 85% over the whole length, is at least 90% over the whole length, is at least 95% over the whole length, is at least 98% over the whole length, or is at least 99% over the whole length of the respective reference module A, C, or Q. It is further particularly preferred that the sequence identity is at least 80% over a continuous stretch of at least 5, 10, 15, 18, 20, 24, 28, or 30 amino acids, is at least 85% over a continuous stretch of at least 5, 10, 15, 18, 20, 24, 28, or 30 amino acids, is at least 90% over a continuous stretch of at least 5, 10, 15, 18, 20, 24, 28, or 30 amino acids, is at least 95% over a continuous stretch of at least 5, 10, 15, 18, 20, 24, 28, or 30 amino acids, is at least 98% over a continuous stretch of at least 5, 10, 15, 18, 20, 24, 28, or 30 amino acids, or is at least 99% over a continuous stretch of at least 5, 10, 15, 18, 20, 24, 28, or 30 amino acids of the respective reference module A, C, or Q.

A fragment (or deletion variant) of module A, C, or Q has preferably a deletion of up to 1, 2, 3, 4, 5, 6, 7, 8, 9, 10, 11, 12, 13, 14, or 15 amino acids at its N-terminus and/or at its C-terminus. The deletion can also be internally.

Additionally, the module A, C, or Q variant or fragment is only regarded as a module A, C, or Q variant or fragment within the context of the present invention, if the modifications with respect to the amino acid sequence on which the variant or fragment is based do not negatively affect the ability of the silk polypeptide to avoid or reduce the formation of a biofilm. The skilled person can readily assess whether the silk polypeptide comprising a module A, C, or Q variant or fragment is still capable of avoiding or reducing the formation of a biofilm, e.g. by coating a substrate with a composition comprising a silk polypeptide comprising a module A, C, or Q variant or fragment and a solvent, by incubating the coated substrate with a microbial solution and by making cell count measurements or optical density (OD) measurements (see example described above and experimental section).

Preferably, the biopolymer is a (recombinant) polypeptide comprising at least one non-repetitive (NR) unit. The biopolymer may be a (recombinant) silk polypeptide comprising at least one non-repetitive (NR) unit. It is preferred that the NR unit is selected from the group consisting of NR3 (SEQ ID NO: 5) or variants thereof, NR4 (SEQ ID NO: 6) or variants thereof, NR5 (SEQ ID NO: 7) or variants thereof, and NR6 (SEQ ID NO: 8) or variants thereof. The NR3 (SEQ ID NO: 5) unit is based on the amino acid sequence of ADF-3 of the spider *Araneus diadematus* and the NR4 (SEQ ID NO: 6) unit is based on the amino acid sequence of ADF-4 of the spider *Araneus diadematus* (WO 2006/008163). In addition, the NR5 (SEQ ID NO: 7) unit and the NR6 (SEQ ID NO: 8) unit is derived from *Latrodectus hesperus.*

A NR3, NR4, NR5, or NR6 unit variant differs from the reference NR3, NR4, NR5, or NR6 unit from which it is derived by up to 1, 2, 3, 4, 5, 6, 7, 8, 9, 10, 11, 12, 13, 14, 15, 16, 17, 18, 19, 20, 25, or 30 amino acid changes in the amino acid sequence (i.e. exchanges, insertions, deletions, N-terminal truncations and/or C-terminal truncations). Such a NR3, NR4, NR5, or NR6 unit variant can alternatively or additionally be characterised by a certain degree of sequence identity to the reference NR3, NR4, NR5, or NR6 unit from which it is derived. Thus, a NR3, NR4, NR5, or NR6 unit variant has a sequence identity of at least 50%, 55%, 60%, 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or even 99.9% to the respective reference NR3, NR4, NR5, or NR6 unit. Preferably, the sequence identity is over a continuous stretch of at least 10, 20, 30, 40, 50, 60, 70, 80, 90, or more amino acids, preferably over the whole length of the respective reference NR3, NR4, NR5, or NR6 unit.

A fragment (or deletion variant) of a NR3, NR4, NR5, or NR6 unit has preferably a deletion of up to 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, or 60 amino acids at its N-terminus and/or at its C-terminus. The deletion can also be internally.

Additionally, the NR3, NR4, NR5, or NR6 unit variant or fragment is only regarded as a NR3, NR4, NR5, or NR6 unit variant or fragment within the context of the present invention, if the modifications with respect to the amino acid sequence on which the variant or fragment is based do not negatively affect the ability of a silk polypeptide to avoid or reduce the formation of a biofilm. The skilled person can readily assess whether the silk polypeptide comprising a NR3, NR4, NR5, or NR6 unit variant or fragment is still capable of avoiding or reducing the formation of a biofilm, e.g. by coating a substrate with a composition comprising a silk polypeptide comprising a NR3, NR4, NR5, or NR6 unit variant or fragment and a solvent, by incubating the coated substrate with a microbial solution and by making cell count measurements or optical density (OD) measurements (see example described above and experimental section).

More preferably, the biopolymer is a (recombinant) silk polypeptide, wherein the silk polypeptide is selected from the group consisting of $(C)_m$, $(C^{Cys})_m$, $(C)_m C^{Cys}$, $(C)_m NR_z$, $NR_z(C)_m$, $NR_z(C)_m NR_z$, $(AQ)_m$, and $(AQ)_m NR_z$, wherein m is an integer of 8 to 96, i.e. 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95 or 96, z is an integer of 1 to 3, i.e. 1, 2, or 3, and NR stands for a non-repetitive unit.

Most preferably, the biopolymer is a (recombinant) silk polypeptide, wherein the silk polypeptide is selected from the group consisting of $C_{16}NR4$, $C_{32}NR4$, $(AQ)_{12}NR3$, $(AQ)_{24}NR3$, $(AQ)_{12}$, $(AQ)_{24}$, $C_{16}$, $C_{32}$, $C_{48}$, $C_{16}C^{Cys}$, $C_{32}C^{Cys}$, and $C_{48}C^{Cys}$.

The first aspect of the present invention, as described above, can alternatively be worded as follows: In a first aspect, the present invention relates to the use of a biopolymer for rendering a substrate, particular a substrate surface, biofilm-repellent.

In a second aspect, the present invention relates to a method for producing a substrate which avoids or reduces the formation of a biofilm on a surface of said substrate comprising the steps of:

(i) providing a composition comprising a biopolymer and a solvent, and (ii) coating the composition onto the surface of said substrate.

In one embodiment, the method further comprises the step of:

(iii) drying the surface of the substrate coated with the composition.

It will be understood by a skilled person that by carrying out the above method, in particular step (ii), or step (ii) and step (iii), a substrate coated with a biopolymer is produced.

The term "avoids the formation of a biofilm on a surface of said substrate", as used herein, means that no biofilm is formed as compared to a surface of a substrate not coated with a biopolymer. The term "reduces the formation of a biofilm on a surface of said substrate", as used herein, means that less biofilm is formed as compared to a surface of a substrate not coated with a biopolymer. The formation of a biofilm on a surface of said substrate may be reduced by at least 1%, 5%, 10%, 20%, 30%, 40%, 50%, 60%, 70%, 80%, 90%, 95%, 98% or 99%, or by 100% as compared to a surface of a substrate not comprising a biopolymer. Preferably, the formation of a biofilm on a surface of a substrate is reduced by at least 10%. More preferably, the formation of a biofilm is reduced by at least 20%. Even more preferably, the formation of a biofilm is reduced by at least 30%. Most preferably, the formation of a biofilm on a surface of a substrate is reduced by at least 90%, e.g. 100%. In case the substrate is not coated with a biopolymer of the invention, i.e. a biopolymer which avoids or reduces the formation of a biofilm, it may, however, be coated with another biopolymer not having this effect.

The skilled person can easily determine experimentally whether the formation of a biofilm is avoided or reduced on a surface of said substrate, e.g. by cell count measurements or optical density (OD) measurements. In this respect, we like to refer to the experimental section. Preferably, cell count measurements are used.

For example, a surface of said substrate is coated with a biopolymer. The surface of said substrate is then contacted with a microbial solution. As a control, an uncoated substrate is used. The coated substrate and the uncoated substrate (control) are incubated with the microbial solution under the same conditions allowing the formation of a biofilm, e.g. between 5 to 36 hours and between 20° C. (room temperature) and 35° C. After the removal of the microbial solution from the coated substrate and the uncoated substrate (control), the number of microorganism grown on the surface of the coated substrate and the uncoated substrate (control) is determined and compared with each other.

The coating may be a film. The biopolymer to be coated can be in form of an aerosol, a liquid, a paste, a semi-solid, or a solid. The coating is preferably achieved by dip coating and/or spray coating. For example, "dip coating" may take place as follows: (i) immersing a substrate into a container containing a composition comprising a biopolymer and a solvent (ii) incubating the substrate with the composition comprising the biopolymer and the solvent in the tank, e.g. for a period between 0.1 sec to 10 min, (iii) removing the substrate which is coated on its surface with the biopolymer from the composition. The substrate which is coated on its surface with the biopolymer can further be dried, e.g. by force-drying, baking, using a heat chamber, radiation, or a fan (at room temperature or at elevated temperatures). It may also be dried at room temperature or at elevated temperatures. For example, "spray coating" may take place as follows: (i) transferring a composition comprising a biopolymer and a solvent into a spray can, spraying device, or nebulizer, and (ii) distributing the composition comprising the biopolymer and the solvent onto the substrate. The substrate which is coated on its surface with the biopolymer can further be dried, e.g. by force-drying, baking, using a heat chamber, radiation, or a fan (at room temperature or at elevated temperatures). It may also be dried room temperature or at elevated temperatures. In addition, the coating can be applied as a hydrogel, an aerosol, or a liquid and solidifies into a solid coating.

As mentioned above, the coating is formed from a composition comprising a biopolymer and a solvent. The composition can be a solution, a suspension, or an emulsion. The composition can also be a hydrogel. The solution may be an aqueous solution or a buffered aqueous solution. The solvent may be water ($H_2O$), an aqueous buffer, or an organic solvent. The organic solvent may be selected from the group consisting of formic acid and hexafluorisopropanol (HFIP). The concentration of the biopolymer in the composition, e.g. solution, may be in the range of 0.1% (w/v) to 30% (w/v). Preferably, the concentration of the biopolymer in the composition, e.g. solution, is in the range of 0.5% (w/v) to 20% (w/v). More preferably, the concentration of the biopolymer in the composition, e.g. solution, is in the range of 0.5% (w/v) to 10% (w/v). Most preferably, the concentration of the biopolymer in the composition, e.g. solution, is in the range of 0.8% (w/v) to 5% (w/v).

As to the definition of the term "biofilm", the term "biopolymer", the preferred embodiments of the "biopolymer", the definition of the term "surface", the definition of the term "substrate", the preferred embodiments of the "substrate", and the definition of the term "coating", it is referred to the first aspect of the present invention.

The second aspect of the present invention, as described above, can alternatively be worded as follows: In a second aspect, the present invention relates to a method for producing a substrate which is biofilm-repellent comprising the steps of:

(i) providing a composition comprising a biopolymer and a solvent, and (ii) coating the composition onto the surface of said substrate.

In one embodiment, the method further comprises the step of:

(iii) drying the surface of the substrate coated with the composition.

It is particular the substrate surface which is rendered biofilm-repellent.

In a third aspect, the present invention relates to a method for producing a substrate which avoids or reduces the formation of a biofilm on a surface of said substrate comprising the steps of:

(i) providing a composition comprising a biopolymer and a solvent, and (ii) forming said substrate from the composition.

In one embodiment, the method further comprises the step of:

(iii) drying the substrate formed from the composition.

It will be understood by a skilled person that by carrying out the above method, in particular step (ii), or step (ii) and step (iii), a substrate comprising a biopolymer is produced.

The term "avoids the formation of a biofilm on a surface of said substrate", as used herein, means that no biofilm is formed as compared to a surface of a substrate, wherein the substrate does not comprise a biopolymer. The term "reduces the formation of a biofilm on a surface of said substrate", as used herein, means that less biofilm is formed as compared to a surface of a substrate, wherein the substrate does not comprise a biopolymer. The formation of a biofilm on a surface of a substrate may be reduced by at least 1%, 5%, 10%, 20%, 30%, 40%, 50%, 60%, 70%, 80%, 90%, 95%, 98% or 99%, or by 100% as compared to a surface of a substrate not comprising a biopolymer. Preferably, the formation of a biofilm on a surface of a substrate is reduced by at least 10%. More preferably, the formation of a biofilm is reduced by at least 20%. Even more preferably, the formation of a biofilm is reduced by at least 30%. Most preferably, the formation of a biofilm on a surface of a substrate is reduced by at least 90%, e.g. 100%. In case the substrate does not comprise a biopolymer of the invention, i.e. a biopolymer which avoids or reduces the formation of a biofilm, it may, however, comprise another biopolymer not having this effect.

The skilled person can experimentally easily determine experimentally whether the formation of a biofilm is avoided or reduced on a surface of said substrate, e.g. by cell count measurements, optical density (OD) measurements, or other methods such as polymerase chain reaction (PCR). In this respect, we like to refer to the experimental section. Preferably, cell count measurements are used. For example, a substrate comprising a biopolymer is produced. The surface of the substrate comprising the biopolymer is then contacted with a microbial solution. As a control, a substrate which does not comprise a biopolymer is used. The substrate comprising the biopolymer and the substrate which does not comprise the biopolymer (control) are incubated with the microbial solution under the same conditions allowing the formation of a biofilm, e.g. between 5 to 36 hours and/or between 20° C. (room temperature) and 35° C. After the removal of the microbial solution from the substrate comprising the biopolymer and the substrate which does not comprise the biopolymer (control), the number of microorganism grown on the surface of the substrate comprising the biopolymer and the substrate which does not comprise the biopolymer (control) is determined and compared with each other.

In one embodiment, the substrate is formed by extruding, pressing, and/or pouring. The formed substrate may be selected from the group consisting of a fiber, a thread comprising the fiber, a twisted yarn comprising the fiber, and a fabric comprising the fiber.

As mentioned above, the substrate is formed from a composition comprising a biopolymer and a solvent. The composition can be a solution, a suspension, or an emulsion. The composition can also be a hydrogel. The solution may be an aqueous solution, a buffered aqueous solution, or an organic solution. The solvent may be water ($H_2O$), an aqueous buffer, or an organic solvent. The organic solvent may be selected from the group consisting of formic acid and hexafluorisopropanol (HFIP). The concentration of the biopolymer in the composition, e.g. solution, may be in the range of 0.1% (w/v) to 30% (w/v). Preferably, the concentration of the biopolymer in the composition, e.g. solution, is in the range of 0.5% (w/v) to 20% (w/v). More preferably, the concentration of the biopolymer in the composition, e.g. solution, is in the range of 0.5% (w/v) to 10% (w/v). Most preferably, the concentration of the biopolymer in the composition, e.g. solution, is in the range of 0.8% (w/v) to 5% (w/v).

As mentioned above, the substrate is formed from a composition comprising a biopolymer and a solvent. The formed substrate may comprise at least 0.1% (w/v), 1% (w/v), 10% (w/v), 20% (w/v), 30% (w/v), 40% (w/v), 50%

(w/v), 60% (w/v), 70% (w/v), 80% (w/v), 90% (w/v), 95% (w/v), 98% (w/v), 99% (w/v), or 100% (w/v) of the biopolymer. Preferably, the substrate comprises at least 1% (w/v) of the biopolymer. More preferably, the substrate comprises at least 2% (w/v) of the biopolymer. Even more preferably, the substrate comprises at least 10% (w/v) of the biopolymer. Most preferably, the substrate comprises at least 90% (w/v), e.g. 100% (w/v), of the biopolymer. In the latter case, the substrate consists of the biopolymer.

As to the definition of the term "biofilm", the term "biopolymer", the preferred embodiments of the "biopolymer", the definition of the term "surface", the definition of the term "substrate", and the preferred embodiments of the "substrate", it is referred to the first aspect of the present invention.

The third aspect of the present invention, as described above, can alternatively be worded as follows: In a third aspect, the present invention relates to a method for producing a substrate which is biofilm-repellent comprising the steps of:
(i) providing a composition comprising a biopolymer and a solvent, and
(ii) forming said substrate from the composition.

In one embodiment, the method further comprises the step of:
(iii) drying the substrate formed from the composition.

It is particular the substrate surface which is rendered biofilm-repellent.

The invention is further summarized as follows:
1. Use of a biopolymer for reducing the formation of a biofilm.
2. The use of item 1, wherein the formation of the biofilm is reduced on a surface of a substrate.
3. The use of items 1 or 2, wherein the biofilm is an aggregate of microorganisms in which cells adhere to each other and/or to the surface of the substrate.
4. The use of item 3, wherein the microorganisms are selected from the group consisting of bacteria, fungi, algae, and protozoa, or any combination thereof.
5. The use of item 4, wherein the bacteria are from the genus *Escherichia, Pseudomonas, Bacillus*, and/or *Staphylococcus*.
6. The use of any one of items 1 to 5, wherein the biopolymer is in the form of a coating.
7. The use of item 6, wherein the coating is a film.
8. The use of items 6 or 7, wherein the coating is formed from a composition, preferably from a solution or from a hydrogel, comprising the biopolymer and a solvent.
9. The use of item 8, wherein the solvent is selected from the group consisting of water, an aqueous buffer, and an organic solvent.
10. The use of item 9, wherein the organic solvent is selected from the group consisting of formic acid and hexafluorisopropanol (HFIP).
11. The use of any one of items 8 to 10, wherein the concentration of the biopolymer in the composition, preferably in the solution or in the hydrogel, is in the range of 0.1% (w/v) to 30% (w/v), preferably in the range of 0.5% (w/v) to 20% (w/v).
12. The use of any one of items 2 to 11, wherein the substrate is a device.
13. The use of item 12, wherein the device is selected from the group consisting of a medical device, a wastewater treatment device, a heating device, a ventilation device, and an air condition device.
14. The use of item 13, wherein the medical device is selected from the group consisting of an extracorporeal medical device, an implant, and a catheter.
15. The use of item 14, wherein
   (i) the extracorporeal medical device is selected from the group consisting of a life support machine, a heart-lung machine, and a dialysis device, or
   (ii) the implant is selected from the group consisting of a stent, a cochlea implant, a microchip implant, a dental implant, and a soft tissue implant, preferably a silicone implant, more preferably a breast implant.
16. The use of any one of items 2 to 15, wherein the substrate is selected from the group consisting of a synthetic inert substrate, an inorganic inert substrate, and a naturally occurring substrate.
17. The use of item 16, wherein the
   (i) synthetic inert substrate is selected from the group consisting of polyester, polystyrene, polyamide (PA), polyaramid, polytetrafluoroethylene (PTFE), polyethylene (PE), polypropylene (PP), polyurethane (PU), silicone, a mixture of polyurethane and polyethylenglycol (elastane), ultra high molecular weight polyethylene (UHMWPE), and high-performance polyethylene (HPPE),
   (ii) inorganic inert substrate is selected from the group consisting of, glass, carbon, ceramic, metal, sapphire, diamond, and semiconductor, or
   (iii) the naturally occurring substrate is selected from the group consisting of keratin, collagen, cellulose, teeth, bone, skin, and tissue.
18. The use of any one of items 2 to 17, wherein the substrate comprises the biopolymer.
19. The use of item 18, wherein the substrate comprising the biopolymer is selected from the group consisting of a fiber, a thread comprising the fiber, a twisted yarn comprising the fiber, and a fabric/textile comprising the fiber.
20. The use of any one of items 1 to 19, wherein the biopolymer is a polypeptide, preferably a recombinant polypeptide.
21. The use of item 20, wherein the polypeptide is a silk polypeptide.
22. The use of item 21, wherein the silk polypeptide comprises at least two identical repetitive units.
23. The use of item 22, wherein the repetitive units are independently selected from the group consisting of module A (SEQ ID NO: 1) or variants thereof, module C (SEQ ID NO: 2) or variants thereof, module $C^{Cys}$ (SEQ ID NO: 3), and module Q (SEQ ID NO: 4) or variants thereof.
24. The use of any one of items 21 to 23, wherein the silk polypeptide comprises at least one non-repetitive (NR) unit.
25. The use of item 24, wherein the NR unit is selected from the group consisting of NR3 (SEQ ID NO: 5) or variants thereof, NR4 (SEQ ID NO: 6) or variants thereof, NR5 (SEQ ID NO: 7) or variants thereof, and NR6 (SEQ ID NO: 8) or variants thereof.
26. The use of any one of items 21 to 25, wherein the silk polypeptide is selected from the group consisting of $(C)_m$, $(C^{Cys})_m$, $(C)_m C^{Cys}$, $(C)_m NR_z$, $NR_z(C)_m$, $NR_z(C)_m NR_z$, $(AQ)_m$, and $(AQ)_m NR_z$, wherein m is an integer of 8 to 96, z is an integer of 1 to 3, and NR stands for a non-repetitive unit.
27. The use of item 26, wherein the silk polypeptide is selected from the group consisting of $C_{16}NR4$, $C_{32}NR4$, $(AQ)_{12}NR3$, $(AQ)_{24}NR3$, $(AQ)_{12}$, $(AQ)_{24}$, $C_{16}$, $C_{32}$, $C_{48}$, $C_{16}C^{Cys}$, $C_{32}C^{Cys}$, and $C_{48}C^{Cys}$.

28. A method for producing a substrate which reduces the formation of a biofilm on a surface of said substrate comprising the steps of:
   (i) providing a composition comprising a biopolymer and a solvent, and
   (ii) coating the composition onto the surface of said substrate.
29. The method of item 28, wherein the method further comprises the step of:
   (iii) drying the surface of the substrate coated with the composition.
30. The method of items 28 or 29, wherein the coating is achieved by dip coating and/or spray coating.
31. A method for producing a substrate which reduces the formation of a biofilm on a surface of said substrate comprising the steps of:
   (i) providing a composition comprising a biopolymer and a solvent, and
   (ii) forming said substrate from the composition.
32. The method of item 31, wherein the method further comprises the step of:
   (iii) drying the substrate formed from the composition.
33. The method of items 31 or 32, wherein the substrate is formed by extruding, pressing, and/or pouring.
34. The method of any one of items 28 to 33, wherein the solvent is selected from the group consisting of water, an aqueous buffer, and an organic solvent.
35. The method of item 34, wherein the organic solvent is selected from the group consisting of formic acid and HFIP.
36. The method of any one of items 28 to 35, wherein the concentration of the biopolymer in the composition, preferably in the solution or in the hydrogel, is in the range of 0.1% (w/v) to 30% (w/v), preferably in the range of 0.5% (w/v) to 20% (w/v).

BRIEF DESCRIPTION OF THE FIGURE

FIG. 1 shows the reduction of biofilm formation due to the coating with a biopolymer. It particularly shows the reduction of biofilm formation on different substrates (polystyrene, rough textured silicone, polytetrafluorethylene (PTFE) and stainless/chrome steel) coated with an aqueous silk solution, a silk hydrogel, or a formic acid silk solution. A reduction of biofilm formation of 75% (polystyrene coated with a formic acid silk solution), 35% (polystyrene coated with a silk hydrogel), 41% (rough textured silicone coated with an aqueous silk solution), 13% (polytetraflourethylene (PTFE) coated with a formic acid silk solution), 40% (polytetraflourethylene (PTFE) coated with an aqueous silk solution) and 66% (stainless steel coated with a formic acid silk solution) was achieved. To determine the reduction of the biofilm formation, the mean value cell number of 16 samples of each experiment (polystyrene, rough textured silicone, polytetrafluoroethylene (PTFE) and stainless steel substrates coated with a $C_{16}$ protein aqueous solution, $C_{16}$ protein formic acid solution and $C_{16}$ protein hydrogel) was determined and calculated against the mean value cell number of the non-coated substrates. Non-coated substrate corresponds to normal biofilm formation (value of 0%). A reduction of biofilm formation of e.g. 75% is shown as a value of −75%.

EXAMPLES

To determine the formation of a biofilm on a surface of a substrate, cell count measurements were applied. The surface of different substrates (polystyrene, polytetrafluorethylene, silicone, and stainless steel) was coated with a silk biopolymer. The surface of said substrates was then contacted with a microbial solution. As a control, an uncoated substrate was used. The coated substrate and the uncoated substrate (control or blank) were incubated with the microbial solution between 5 to 10 hours at 30° C., allowing the formation of a biofilm. After the removal of the microbial solution from the coated substrate and the uncoated substrate (control or blank), the number of microorganisms grown on the surface of the coated substrate was determined and compared to the number of microorganism grown on the surface of the uncoated substrate (control or blank).

Example 1: Preparation of the Coating Solution/Hydrogel

The $C_{16}$ protein was prepared as described in WO 2006/008163.
a) Preparation of a $C_{16}$ Protein Aqueous Solution:

$C_{16}$ protein was dissolved in 6 M GdmSCN, diluted with 5 mM Tris/HCl pH 8.5 to 0.6 M GdmSCN. The solution was cross-filtrated against 4 M Urea (10-15×) and then cross-filtrated against 5 mM Tris/HCl pH 8.5 (Crossflow; Vivaflow 10-20×) until no urea was detectable.

Alternatively, $C_{16}$ protein was dissolved in 6 M GdmSCN, diluted with 5 mM Tris/HCl pH 8.5 to 0.6 M GdmSCN. The protein solution was cross-filtrated against 5 mM Tris/HCl pH 8.5 (Crossflow Vivaflow 10-20×) until no GdmSCN was detectable.

14 ml of $C_{16}$ protein aqueous solution (C16 protein solution in 5 mM Tris, pH 8.5; protein concentration 12.5 g/l) were filled up to a final volume of 17 ml with deionized water to final protein concentration of 10 g/l.
b) Preparation of a $C_{16}$ Protein Hydrogel:

30 ml of a $C_{16}$ protein solution ($C_{16}$ protein solution in 5 mM Tris, pH 8.5; protein concentration 12.5 g/l) were filled up with 7.5 ml of 5 mM Tris to final protein concentration of 10 g/l. The $C_{16}$ protein solution was then autoclaved in 250 ml Schott-flask (autoclave Systec VX-100) to form a hydrogel.
c) Preparation of $C_{16}$ Protein Formic Acid Solution:

212.9 mg of $C_{16}$ protein (γ-sterilized) were mixed with 21.2 ml of formic acid 98% (Carl-Roth, #4742.2, Lot 42422005) by rotation for a period of 30 min at room temperature resulting in a final protein concentration of 10 g/l.

Alternatively 100 mg of $C_{16}$ protein were dissolved in 10 ml formic acid 98% (Carl-Roth, #4742.2, Lot 42422005) by rotation for a period of 30 min at room temperature resulting in a final protein concentration of 10 g/l.

Example 2: Preparation of the Substrates

The different substrates were prepared as follows:
a) Preparation of the polytetrafluoroethylene (PTFE) substrates: PTFE patches with a diameter of 5 mm were punched out using a commercial perforator and glued to the bottom of a 96 well plate using Sylgard 184 silicone (Swiss-composite).
b) Preparation of the stainless steel substrates: stainless steel patches (Product Nr. FK110250/1, 300649549, GoodFellow) with a diameter of approx. 5 mm were punched out using a commercial perforator, flattened with a hammer and glued to the bottom of a 96 well plate using Sylgard 184 silicone (Swiss-composite).

c) Preparation of polystyrene substrates: the untreated wells of a polystyrene 96-well plate were used as substrate.

For coating of the polytetrafluorethylene, stainless steel and polystyrene substrates with a $C_{16}$ protein hydrogel, 75 µl of a 1% $C_{16}$ protein hydrogel were pipetted into the wells of a 96-well plate and dried overnight. The next day, 50 µl of methanol were pipetted in each well and dried at 60° C. in oven. The resulting wells were homogeneously coated with a thin film. Untreated wells were used as control.

For coating of the polytetrafluorethylene, stainless steel and polystyrene substrates with a $C_{16}$ protein aqueous solution, 120 µl of 1% $C_{16}$ protein aqueous solution were pipetted into the wells of the plate and dried overnight. The next day, 50 µl of methanol were pipetted in each well and dried at 60° C. in oven. The resulting wells were homogeneously coated with a transparent thin film. Untreated wells were used as control.

For coating of the polytetrafluorethylene, stainless steel and polystyrene substrates with a $C_{16}$ protein formic acid solution, 70 µl of 1% $C_{16}$ protein formic acid solution were pipetted into the wells of a 96-well plate and dried overnight. The resulting wells were homogeneously coated with a transparent thin film. Untreated wells were used as control.

d) Preparation of silicone substrates (rough-textured):

For the coating of textured silicone patches with a $C_{16}$ protein aqueous solution, silicone patches were cut out from a textured silicone foil to a diameter fitting into the wells and subsequently washed with ethanol. The silicone patches were attached to a glass slide and dip-coated into the $C_{16}$ protein aqueous solution. Therefore the glass slides with attached silicone patches were dipped into the 1% $C_{16}$ protein aqueous solution for a period of 2 min and subsequently dried for a period of 5 min. This step of dipping and drying was repeated three times. The glass slides with attached silicone patches were dried for a period of 5 min at 60° C. Then the glass slides with attached silicone patches were dipped into phosphate buffer (0.5 M $Na_2HPO_4$/$NaH_2PO_4$ for a period of 30 s and dried for a period of 30 s. After a washing step with deionized $H_2O$ (10 s) and a drying step (30 s) the silicone substrates were removed from the glass slides and glued to the bottom of the wells of a polystyrene 96-well plate using Sylgard 184 silicone (Swiss-composite). Untreated silicone patches served as a control.

For the coating of textured silicone patches with a $C_{16}$ protein formic acid solution, silicone patches were attached to a glass slide and dip-coated into the $C_{16}$ protein formic acid solution. Therefore the glass slides with attached silicone patches were dipped into the 1% $C_{16}$ protein formic acid solution for a period of 2 min and subsequently dried for a period of 5 min. This step of dipping and drying was repeated three times. The glass slides with attached silicone patches were dried for a period of 5 min at 60° C. Then the silicone substrates were removed from the glass slides and glued to the bottom of the wells of a polystyrene 96-well plate using Sylgard 184 silicone (Swiss-composite). Untreated silicone patches served as a control.

For the coating of textured silicone patches with a $C_{16}$ protein hydrogel, silicone patches were cut out from a textured silicone foil to a diameter fitting into the wells and subsequently washed with ethanol. The silicone patches were glued to the bottom of the wells of a polystyrene 96-well plate using Sylgard 184 silicone (Swiss-composite). The silicone patches were coated by pipetting 75 µl of a 1% $C_{16}$ protein hydrogel onto a silicone patch and dried overnight. The next day, 50 µl of methanol were pipetted on each patch and dried in oven at 60° C. The resulting wells were homogeneously coated with a thin film. Untreated silicone patches glued to the bottom of the 96-well plate served as a control.

Example 3: Determination of the Biofilm Formation on Different Coated Substrates In order to test the biofilm formation, polystyrene 96-well plates (Greiner bio-one, PS, flat bottom) assembled with different substrates (polystyrene, rough textured silicone, polytetrafluorethylene (PTFE) and stainless steel) were coated with the silk biopolymer according to example 2. As a control, uncoated substrates were used. The 96-well plates were incubated with an adherent bacterial culture of biofilm-forming bacteria (*Staphylococcus aureus*). After incubation, the number of bacterial cells grown on the 96 well plates was determined and compared to the number of bacterial cells grown on the respective substrates without silk biopolymer coating.

In particular, an inoculum of 200 µl of *Staphylococcus aureus* in culture medium (0.5% TSB (tryptic soy broth) with yeast peptone dextrose) was added to the 96-well plates. Culture medium (0.5% TSB (tryptic soy broth) with yeast peptone dextrose without *Staphylococcus aureus* was used as control. After incubation on a microtiter plate shaker (100 rpm, 6 h), the supernatant was removed and the wells were carefully washed three times with physiological NaCl solution. Following the removal of the supernatant, 150 µl of NaCl solution were added to each well and the plate was mixed thoroughly (10 min, Vortex) to remove the adherent bacterial cells. After a dilution series the cells were spotted on tryptic soy agar square plates and grown for a period of 16 to 24 hours at 33° C. The determination of cell numbers was made by counting the colonies with the help of a binocular.

Figure 1:
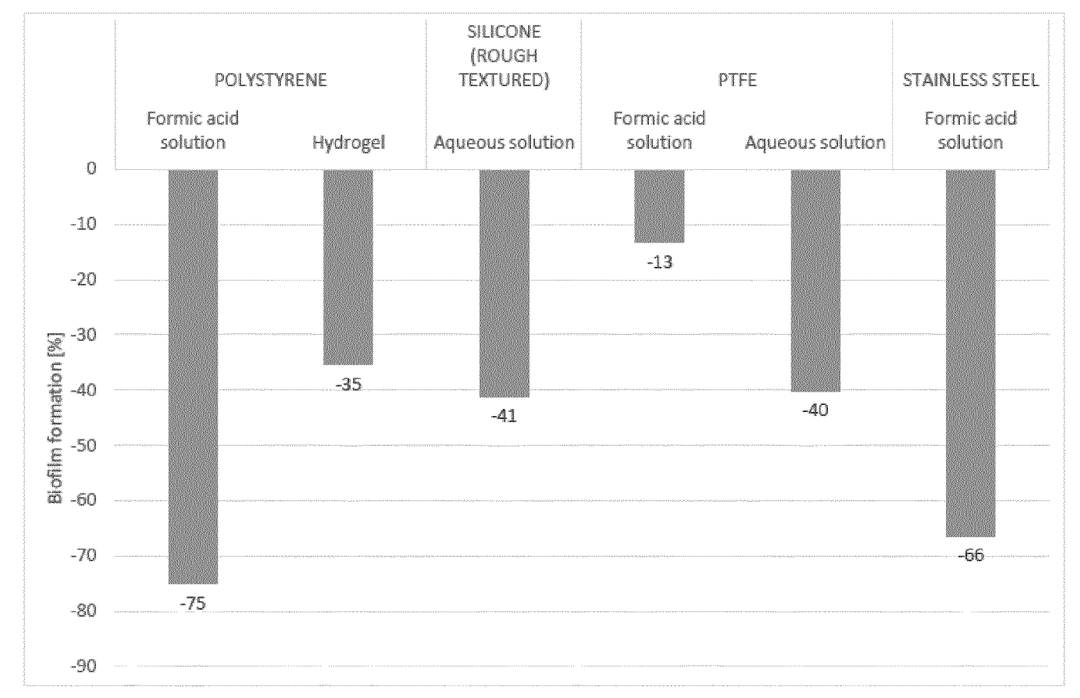

To determine the reduction of the biofilm formation, the mean value cell number of 16 samples of each experiment (polystyrene, rough textured silicone, polytetrafluorethylene (PTFE) and stainless steel substrates coated with a $C_{16}$ protein aqueous solution, $C_{16}$ protein formic acid solution and $C_{16}$ protein hydrogel) was determined and calculated against the mean value cell number of the non-coated substrates. FIG. 1 shows the reduction of biofilm formation on different substrates (polystyrene, rough textured silicone, polytetrafluorethylene (PTFE) and stainless steel) coated with an aqueous silk solution (aqueous solution), a silk hydrogel (hydrogel) and a formic acid silk solution (formic acid). A reduction of biofilm formation of 75% (polystyrene coated with a formic acid silk solution; column 1), 35% (polystyrene coated with a silk hydrogel; column 2), 41% (rough textured silicone coated with an aqueous silk solution; column 3), 13% (polytetrafluorethylene (PTFE) coated with a formic acid silk solution; column 4), 40% (polytetrafluorethylene (PTFE) coated with an aqueous silk solution; column 5) and 66% (stainless steel coated with a formic acid silk solution; column 6) was achieved.

Example 4: Determination of Biofilm Formation on a Biopolymer Textile Substrate Compared to a Polyester Textile Substrate and a Silk-Coated Silicone Foil Compared to a Non-Coated Silicone Foil In this example, biofilm formation on a biopolymer textile substrate compared to a polyester textile substrate was determined. The biopolymer textile substrate was a silk biopolymer textile substrate. The silk biopolymer was composed of 100% $C_{32}NR4$ silk protein. The silk protein was prepared as described in WO 2006/008163. The protein was then processed into fibers as described in WO 2014/037453. Three multifilaments were twisted into a yarn using a ring twisting machine. This yarn was taken for the kitting process. A 2D-pattern was knitted out of this yarn material. The resulting silk biopolymer textile was cut into three 5 cm×5 cm samples and sterilized by autoclaving.

In addition, biofilm formation on a silk-coated silicone foil compared to a non-coated silicone foil was determined. Three samples of silicone foil (5 cm×5 cm) were coated with 1% $C_{16}$ silk hydrogel. Therefore, the samples sterilized by autoclaving were incubated in 20 ml 1% $C_{16}$ silk hydrogel for 5 minutes. The silk hydrogel was prepared as described in example 2. After incubation, the samples were dried over night at RT under sterile conditions. Three samples of uncoated silicone foil (5 cm×5 cm sterilized by autoclaving) were used as control.

Three samples of uncoated polyester were used as PES test textile. Therefore, three polyester multifilaments (TWD Fibres GmbH, Deggendorf) were processed into a knitted fabric. The resulting polyester textile was cut into three 5 cm×5 cm samples.

In order to determine the reduction of the biofilm formation, a thin liquid film (400 µl) containing the bacteria *Staphylococcus epidermidis* DSM 18857 (Leibniz Institute DSMZ-German Collection of Microorganisms and Cell Cultures) ($1.25 \times 10^4$ cells/cm$^2$) were applied to four different substrate samples (5 cm×5 cm, in triplicates): polyester uncoated (PES test textile), silk biopolymer textile, textured silicone foil uncoated, textured silicone foil coated with silk biopolymer. The substrate samples coated with the liquid film containing the bacteria were subsequently covered with a foil ("Stomacher-Bags") to prevent desiccation. Immediately after application of the liquid film containing the bacteria, a zero sample was collected from the surface of the substrates and the covering foil by vortexing or sonification in PBS to determine the bacterial count (CFU) (tovalue). The zero samples and the substrate samples (polyester uncoated, biopolymer textile, textured silicone foil uncoated, textured silicone foil coated with silk biopolymer) were further incubated in the liquid film containing the bacteria under humid conditions at 37° C. After 24 h, the bacteria were collected from the surface of the substrate samples and the covering foil by vortexing or sonification in PBS. The bacterial cells were plated to determine the bacterial count (CFU) ($t_{24}$-value). The results are shown in table 1.

Table 1 shows that the biopolymer textile results in a reduction of biofilm formation of more than 99.99% compared to uncoated polyester. In other words, the formation of a biofilm on the biopolymer textile was almost completely avoided. With the silk coated silicone foil, a reduction of biofilm formation of 93.16% could be determined compared to uncoated silicone foil.

Example 5: Determination of the Biofilm Formation on Cotton Fabric and Polyester Fabric Compared to Silk Biopolymer Fabric (In Vitro and In Vivo)

In this example, the biofilm formation on cotton fabric and polyester fabric compared to silk biopolymer fabric (in vitro and in vivo) was determined. The silk biopolymer fabric sample was composed of 100% $C_{32}NR4$ silk protein. The silk protein was prepared as described in WO 2006/008163. The protein was then processed into fibers as described in WO 2014/037453. Three multifilaments were twisted into a yarn using a ring twisting machine. This yarn was taken for the weaving process. The yarn was used in direction of warp and weft while weaving a fabric size of A4. The fabric was cut into 1.5 cm×1.5 cm samples.

In order to determine the reduction of the biofilm formation on cotton fabric and polyester fabric compared to biopolymer fabric in vitro, two samples of each fabric (1.5 cm×1.5 cm, sterilized by autoclaving) were incubated in 10 ml ($4.3 \times 10^4$ cells/ml in CASO-broth bacterial solution containing *Staphylococcus arlettae* DSM 30634 (Leibniz Institute DSMZ-German Collection of Microorganisms and Cell Cultures) at room temperature (RT) for 5-6 hours with agitation. After incubation, the fabric samples were washed twice in PBS (first washing step: 10 ml PBS with agitation at 60 rpm for 5 min, second washing step: 10 ml PBS with agitation for 1 min). After the first and second washing step, PBS was removed from the samples by dabbing the fabric samples on sterilized tissue paper. The fabric samples were applied to CASO agar plates. After incubation of the plates for 48 h at 37° C. and for 36 h at RT (room temperature), the number of bacterial colonies was determined by optical inspection. The sample with the highest bacterial growth was set 100%. The sample with the lowest/no bacterial growth was set 0%. Fabric samples sterilized by autoclaving were used as a negative control. The results are shown in Table 2.

TABLE 1

| Sample | $t_0$ [cells/cm$^2$] | | | $t_{24}$ [cells/cm$^2$] | | |
|---|---|---|---|---|---|---|
| Polyester uncoated | $1.0 \times 10^4$ | $1.2 \times 10^4$ | $1.2 \times 10^4$ | $1.6 \times 10^3$ | $2.1 \times 10^3$ | $1.2 \times 10^3$ |
| Silk biopolymer textile | | | | $<1 \times 10^1$ | $<1 \times 10^1$ | $<1 \times 10^1$ |
| Silicone foil uncoated | $1.0 \times 10^4$ | $1.0 \times 10^4$ | $1.0 \times 10^4$ | $1.1 \times 10^3$ | $1.3 \times 10^3$ | $7.9 \times 10^2$ |
| Silicone foil coated with silk biopolymer | | | | $9.6 \times 10^1$ | $4.8 \times 10^1$ | $7.2 \times 10^1$ |

TABLE 2

Biofilm formation on different fabric samples:

|  | Sample 1 | Sample 2 |
|---|---|---|
| Cotton | 4 | 4 |
| Polyester | 4 | 4 |
| Silk Biopolymer | 0 | 0 |
| Negative Control | 0 | 0 |

Table 2 shows that no biofilm formation could be detected on silk fabric, whereas cotton fabric and polyester fabric exhibit strong biofilm formation. The following symbols represent the biofilm formation: 4: 100%, 3: 75%, 2: 50%, 1: 25%, 0: 0% (no biofilm formation)

In order to determine the reduction of the biofilm formation on cotton fabric and polyester fabric compared to silk biopolymer fabric in vivo, five samples of each fabric (1.5 cm×1.5 cm, sterilized by autoclaving) were applied to human skin. Therefore, the fabric samples were fixed to the human skin of five different test persons with the aid of a plaster for period of 8 hours. After removing the plasters with the fabric samples from the skin of the test persons, the fabric samples were washed twice in PBS (first washing step: 10 ml PBS with agitation at 60 rpm for 5 min, second washing step: 10 ml PBS with agitation for 1 min). After the first and second washing step, PBS was removed from the samples by dabbing samples on sterilized tissue paper. The skin facing side of the fabric samples were placed onto CASO agar plates. After incubation at RT for 36 h, the number of bacterial colonies was determined by optical inspection. The sample with the highest bacterial growth was set 100%. The sample with the lowest/no bacterial growth was set 0%. Fabric samples sterilized by autoclaving were used as a negative control. The results are shown in Table 3.

TABLE 3

Biofilm formation on different subjects (in vivo):

|  | Subject 1 | Subject 2 | Subject 3 | Subject 4 | Subject 5 |
|---|---|---|---|---|---|
| Cotton | 3 | 1 | 3 | 4 | 2 |
| Polyester | 4 | 3 | 1 | 2 | 3 |
| Silk Biopolymer | 0 | 0 | 0 | 0 | 0 |
| Negative control | 0 | 0 | 0 | 0 | 0 |

Table 3 shows that no biofilm formation after application to human skin could be detected on silk biopolymer fabric, whereas cotton fabric and polyester fabric exhibit weak to strong biofilm formation. The following symbols represent the biofilm formation: 4: 100%, 3: 75%, 2: 50%, 1: 25%, 0: 0% (no biofilm formation)

Example 6: Determination of the Biofilm Formation on Non-Coated Polyester Fabric Compared to Polyester Fabric Coated with Silk Biopolymer In this example, the biofilm formation on non-coated polyester fabric was compared to polyester fabric coated with silk biopolymer. The polyester fabric samples used for the comparative test were coated with 1% $C_{16}$ silk hydrogel. Therefore, the samples sterilized by autoclaving were incubated in 20 ml 1% $C_{16}$ silk hydrogel for 5 minutes. The silk hydrogel was prepared as described in example 2. After dipping, the samples were dried over night at RT under sterile conditions.

In order to determine the reduction of the biofilm formation on non-coated polyester fabric compared to polyester fabric coated with biopolymer in vivo, two samples of uncoated polyester fabric (1.5 cm×1.5 cm, sterilized by autoclaving) and two samples of silk-coated fabric were applied to human skin. Therefore, the fabric samples were fixed to the human skin of four different test persons with the aid of a plaster for period of 8 hours. After removing the plasters with the fabric, samples from the skin of the test persons the fabric samples were washed twice in PBS (first washing step: 10 ml PBS with agitation at 60 rpm for 5 min, second washing step: 10 ml PBS with agitation for 1 min). After the first and second washing step, PBS was removed from the fabric samples by dabbing the samples on sterilized tissue paper. The skin facing side of the fabric samples were placed onto CASO agar plates. After incubation for 48 h at 37° C. and for 36 h at RT, the number of bacterial colonies was determined by optical inspection. The sample with the highest bacterial growth was set 100%. The sample with the lowest/no bacterial growth was set 0%. Fabric samples sterilized by autoclaving were used as a negative control. The results are shown in Table 4.

TABLE 4

Biofilm formation on non-coated polyester fabric compared to polyester fabric coated with biopolymer (in vivo):

|  | Subject 1 | Subject 2 | Subject 3 | Subject 4 |
|---|---|---|---|---|
| Polyester uncoated | 4 | 3 | 1 | 2 |
| Polyester coated | 0 | 0 | 0 | 0 |
| Negative control | 0 | 0 | 0 | 0 |

Table 4 shows that no biofilm formation on silk coated polyester fabric after application to human skin could be detected, whereas uncoated polyester fabric exhibit weak to strong biofilm formation. The following symbols represent the biofilm formation: 4: 100%, 3: 75%, 2: 50%, 1: 25%, 0: 0% (no biofilm formation).

The invention claimed is:

1. A method for reducing the formation of a biofilm on a substrate, comprising the step of:
applying a composition consisting essentially of a silk polypeptide and a solvent on the surface of a substrate to form a silk polypeptide coating on the surface or producing a substrate from a composition consisting essentially of a silk polypeptide and a solvent, thereby reducing the formation of a biofilm on the substrate.

2. The method of claim 1, wherein the biofilm is an aggregate of microorganisms in which cells adhere to each other and/or to the surface of the substrate, wherein the microorganisms are selected from the group consisting of bacteria, fungi, algae, protozoa, and any combination thereof.

3. The method of claim 1, further comprising drying the surface of the substrate after the composition is applied on the surface of the substrate.

4. The method of claim 1, wherein the substrate is a device.

5. The method of claim 4, wherein the device is selected from the group consisting of a medical device, a wastewater treatment device, a heating device, a ventilation device, and an air condition device.

6. The method of claim 1, wherein the substrate is selected from the group consisting of a synthetic inert substrate, an inorganic inert substrate, and a naturally occurring substrate.

7. The method of claim 6, wherein the
(i) synthetic inert substrate is selected from the group consisting of polyester, polystyrene, polyamide (PA), polyaramid, polytetrafluorethylene (PTFE), polyethylene (PE), polypropylene (PP), polyurethane (PU), silicone, a mixture of polyurethane and polyethylenglycol (elastane), ultra high molecular weight polyethylene (UHMWPE), and high-performance polyethylene (HPPE),
(ii) inorganic inert substrate is selected from the group consisting of, glass, carbon, ceramic, metal, sapphire, diamond, and semiconductor, or
(iii) the naturally occurring substrate is selected from the group consisting of keratin, collagen, cellulose, teeth, bone, skin, and tissue.

8. The method of claim 1, further comprising drying the substrate after the substrate is produced from the composition.

9. The method of claim 1, wherein the silk polypeptide is a recombinant silk polypeptide.

10. A method for producing a substrate which reduces the formation of a biofilm on a surface of said substrate comprising the steps of:
(i) providing a composition consisting essentially of a silk polypeptide and a solvent, and
(ii) coating the composition onto the surface of said substrate to form a silk polypeptide coating on the surface.

11. The method of claim 10, wherein the method further comprises the step of:
(iii) drying the surface of the substrate coated with the composition.

12. A method for producing a substrate which reduces the formation of a biofilm on a surface of said substrate comprising the steps of:
(i) providing a composition consisting essentially of a silk polypeptide and a solvent, and
(ii) forming said substrate from the composition.

13. The method of claim 12, wherein the method further comprises the step of:
(iii) drying the substrate formed from the composition.

14. A method for reducing the formation of a biofilm on a substrate, comprising the step of:
applying a composition consisting of a silk polypeptide and a solvent on the surface of a substrate to form a silk polypeptide coating on the surface or producing a substrate from a composition consisting of a silk polypeptide and a solvent, thereby reducing the formation of a biofilm on the substrate.

* * * * *